United States Patent [19]

Schultz

[11] Patent Number: 4,688,560

[45] Date of Patent: Aug. 25, 1987

[54] SURGICAL WIRE CAP AND METHOD OF USING SAME

[76] Inventor: Robert J. Schultz, 229 E. Hunting Ridge Rd., Stamford, Conn. 06903

[21] Appl. No.: 814,914

[22] Filed: Dec. 30, 1985

[51] Int. Cl.⁴ ............................................. A61F 5/04
[52] U.S. Cl. ................................................ 128/92 YE
[58] Field of Search ....... 128/92 YR, 92 YW, 92 YE, 128/92 YM

[56] References Cited

U.S. PATENT DOCUMENTS

| | | | |
|---|---|---|---|
| 2,631,584 | 3/1953 | Purificato | 128/92 YW |
| 3,602,218 | 8/1971 | Riordan et al. | 128/92 YE |
| 3,809,075 | 5/1974 | Matles | 128/92 YF |
| 4,537,185 | 8/1985 | Stednitz | 128/92 YE |

*Primary Examiner*—C. Fred Rosenbaum
*Assistant Examiner*—C. W. Shedd
*Attorney, Agent, or Firm*—McAulay, Fields, Fisher, Goldstein & Nissen

[57] ABSTRACT

Wires are employed for the setting of fractured bones, or for stabilization of bones making up a joint. A portion of the wire protrudes from at least one of the bone segments and, to prevent movement or loss of these wires, and to prevent injury to surrounding tissue, other persons, or clothing, by the exposed ends, caps are provided which are easily secured to the ends and graspable for removal of the wire, when desired. In some cases, the ends of the wire may protrude through the skin and the caps are attached externally.

4 Claims, 8 Drawing Figures

U.S. Patent  Aug. 25, 1987  4,688,560
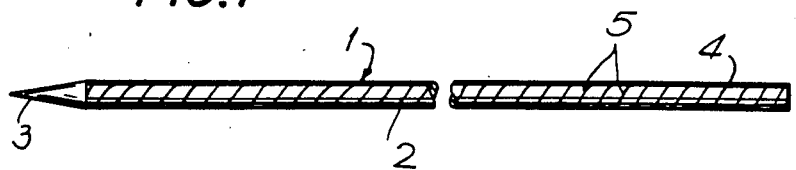
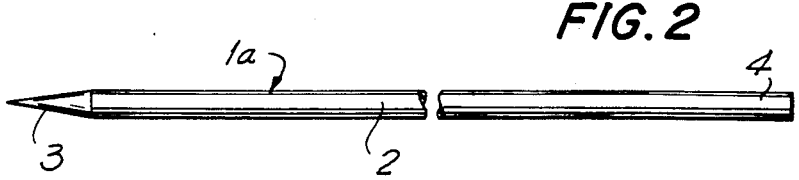
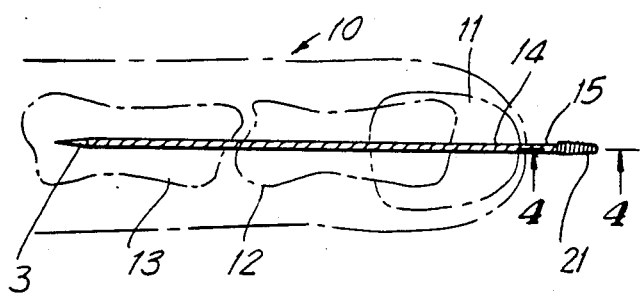
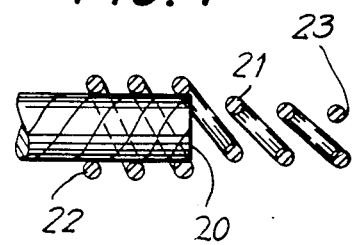
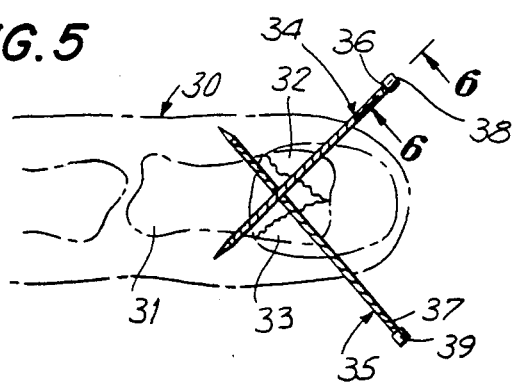
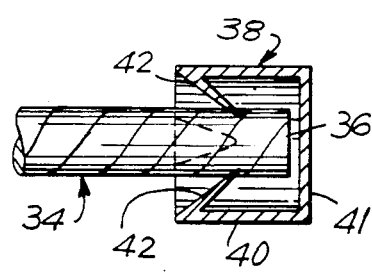
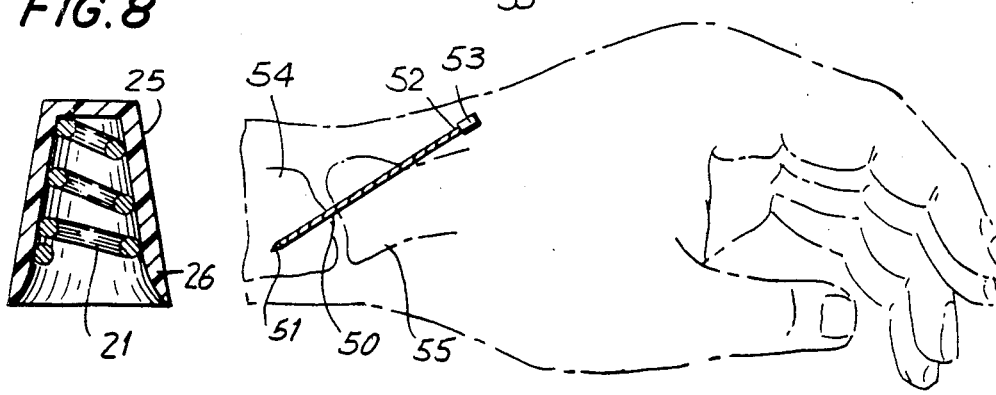

SURGICAL WIRE CAP AND METHOD OF USING SAME

BACKGROUND OF THE INVENTION

In the setting of fractured bones, the diverse pieces of bone are frequently held together by strong, narrow wires. Such strong narrow wires are also used in operations involving joints, where the joint position must be maintained during the healing process. A prominent type of wire used in the medical field for this purpose is known as a Kirshner wire, which is a thin wire, of varying length, and generally available in diameters of 0.037; 0.045; and 0.067 inch. The correct diameter is selected based upon the particular use. Steinman pins, which are similar to Kirshner wires, but of larger diameter, are used for the same purpose and throughout this specification the term "Kirshner wire" or "wires" will be understood to mean Kirshner wires, Steinman pins, and any similar product.

One or both ends of these Kirshner wires are pointed to aid in placement of the wire into the bone and the surface of the wire may be smooth or threaded. Whichever type of wire is employed, it is cut to the desired length, and this length may be such that the entire wire, including the cut end, is below the skin level, or the wire may be of such a length that the cut end protrudes through the skin.

The use of these wires, however, is subject to at least three disadvantages:

1. The wires may tend to migrate from their original position where they were placed to hold portions of bones together or to position a joint on which an operation has been performed, and, at times, migrate to parts of the body where severe injury can be caused;

2. Because of the sharp ends, when the Kirshner wires protrude through the skin, the sharp end can present a danger to surrounding tissues, apparel, and other individuals;

3. Even if the wire has not moved after its original placement, and, particularly, if it is totally beneath the surface of the skin, because of its small size, it may frequently be difficult to locate when removal of the wire is desired after completion of the healing process.

In accordance with the present invention, a cap has been developed for placement over the end of a Kirshner wire, the cap limiting movement of the wire from its original position and also assisting in location of the wire for removal upon completion of the healing process. Further, use of this cap prevents injury which might otherwise be caused by an exposed wire protruding through the skin.

SUMMARY OF THE INVENTION

The present invention is not directed to the general usage of Kirshner wires in the medical field and, in accordance with the present invention, such wires are employed in their normal manner. Thus, such wires can be employed for joining together two pieces of bone or for holding a joint in a preselected position, generally following an operation. Rather, the present invention is directed to the treatment afforded the exposed end of the wire, such as a Kirshner wire. This treatment can be applied to the exposed end whether it protrudes through the skin, or whether it is entirely internal.

If the end of the wire, whether it protrudes through the skin, or is left below the skin level, has excess length, this excess length is cut off. A cap is then placed over this end to limit movement of the wire inwardly and/or to prevent injury to surrounding tissues, apparel, and others. Further, where the wire is entirely below the skin, the cap can be used to assist in location of the wire when removal of the wire, following a healing process, is indicated.

The cap can take a variety of forms and shapes. For example, the cap can take the form of a wire coil with a diameter decreasing from an open end to a closed end, such as the insert in an object frequently used for joining of electrical wires, as in a junction box, and known as a wire nut. The wire nut may be surrounded by a metal or plastic cover which also provides a skirt member. Further, the cap can be a hollow member, with a closed top, and prongs projecting internally and inwardly, as in an acorn or Tinnerman nut.

BRIEF DESCRIPTION OF THE DRAWINGS

In the accompanying drawings:

FIG. 1 is a sectional view of a wire for joining pieces of bone, partially broken away, showing a single pointed end and threading on the surface;

FIG. 2 is a view similar to FIG. 1 showing a plain surface on the wire;

FIG. 3 is a sectional view, partially broken away, showing a bone setting wire in place for joining two pieces of bone as in a joint operation, the exposed end of the wire being fitted with a wire nut;

FIG. 4 is an exploded view along the line 4—4 of FIG. 3;

FIG. 5 is a sectional view, partially broken away, of two wires being employed for holding together pieces of a fractured bone, the exposed ends of said wires being provided with pronged nuts;

FIG. 6 is an exploded view along the line 6—6 of FIG. 5;

FIG. 7 is a view showing a wire with a pronged nut within the skin shown for holding a joint in place.

FIG. 8 is a sectional view of a wire nut, in accordance with the present invention, surrounded by a cover, with a depending skirt.

DESCRIPTION OF THE PREFERRED EMBODIMENTS

When a bone is fractured, the pieces must be set in the proper juxtaposition to allow for the healing process to take place. With bone damage, this generally involves the continued growth of two pieces of bone so that the pieces are again together. Such a procedure is also required in, for example, joint surgery and similar procedures where the bones of the joint must be held in a proper position following surgery to allow for proper healing.

In order to maintain the position of the bones during the healing process, wires are often employed to hold the pieces of bone, or the members of the joint, in the proper position, these wires being inserted through various pieces of the skeletal structure. Such wires, such as Kirshner wires, come in a variety of diameters and lengths; the diameter and length chosen are dependent upon the particular bone or joint being treated.

As illustrated in FIG. 1, such wires 1 generally have a straight, central section 2 having a rounded cross section. Particularly to allow for ease of insertion of the wire, the ends 3 are generally pointed. The surface 4 of the wire may be provided with threading 5, or may be smooth as shown by wire 1a in FIG. 2.

FIG. 3 illustrates one type of utilization for the wire of the present invention. Illustrated is a finger 10 including the nail 11. As illustrated, two phalanges 12 and 13 are joined, as in repair of a dislocated joint, to provide for healing. A Kirshner wire 14, such as that illustrated in FIG. 1, is inserted through the two phalanges 12 and 13, one pointed end 3 of the Kirshner wire 14 remaining within phalange 13 and the other end 15 of the Kirshner wire extending out of the end of the finger.

Assuming there is no movement of the Kirshner wire during the healing process, the projection of this portion of the wire beyond the end of the finger can lead to injury, either to the patient, apparel, or others. To prevent this, while still maintaining position and location of the wire, the pointed end extending from the end of the figurer is cut off as illustrated by the blunt end 20 in FIG. 4. Onto the resulting blunt end, a cap, particularly a wire nut 21, in accordance with the present invention, is screwed.

As previously indicated, this wire nut is similar in construction to wire nuts employed in joining electrical conductors. As such, it includes a coil of wire which tapers in diameter from the open end 22 to the closed end 23. As it is screwed onto the Kirshner wire, because of the spring form of the wire nut, it gradually expands, but with ever increasing pressure being exerted upon the wire onto which it is being screwed. Thus, when application has ceased, the nut is tightly held to the end of the wire. In this way, the wire is held in place and migration is prevented because of the presence of the nut, the wire can be more easily located for removal when desired, and because of the presence of the nut, the exposed end of the wire does not provide a hazard.

As shown in FIG. 8, the wire nut 21 may be surrounded by a sheath 25 which provides a depending skirt 26. The sheath 25 may be formed of plastic, or metal, as desired, so long as electrolytic action is avoided. In this form, the wire nut is similar to the commercial form of the product sold for joining of electrical wires.

In general, Kirshner wires are manufactured of stainless steel. Because stainless steel does not chemically react with body components, and is generally inert, this is also an acceptable material for the cap. In addition, by forming both the wire and the cap of stainless steel, electrolytic action is avoided. The particular material of which the cap of the present invention is constructed is not critical, so long as it does not react with body components, and as long as it does not provide for electrolytic action with whatever material the wire is formed from.

A second illustration of use of the present invention is given in FIG. 5 where the phalange 30 is not cleanly broken, but is fractured into three pieces 31, 32, and 33. To hold the smaller sections 32 and 33 to the larger piece of the phalange 31, Kirshner wires 34 and 35 are employed. The ends of these wires 36 and 37 protrude from the sides of the finger. Again, in order to be certain of being able to locate the wires, during and following the healing process, and to prevent injury from the exposed ends, caps 38 and 39, in accordance with the present invention, are placed over the ends 36 and 37.

An exploded view of the caps 38 and 39, attached to the wires 34 and 35, is shown in FIG. 6. Since the views are identical, FIG. 6 is directed to the wire 34 having a blunted end 36 to which a cap 38 has been attached. The blunted end 36 is formed, of course, by cutting off the end of a Kirshner wire, such as the wire illustrated in FIG. 1. As shown in FIG. 6, the cap consists of a cylindrical skirt 40 which is integral with a flat end 41. Extending inwardly, at an angle, from the opposite end of the skirt 40 are a plurality of prongs 42. The cap 38 is forced over the wire 34 which engages prongs 42. Because of the angling of these prongs 42, any attempt to remove the cap 38 from the wire 34 is met by resistance from the prongs which tend to attempt to force themselves into the surface of the wire 34, thus providing a resistance to removal of the cap 38.

FIG. 7 shows a further utilization of a wire 50, of the type illustrated in FIG. 1, having a pointed end 51 and a blunted end 52 within cap 53. This wire is meant to maintain the orientation of bones 54 and 55 within a wrist, following surgery. There was not, necessarily, any breakage of the bones 54 and 55 prior to insertion of the pin, but the orientation of these bones within the joint is important during a healing process following surgery. It will also be appreciated that the end 52 of wire 50 and the cap 53 are both below the surface of the skin in FIG. 7, so that the cap 53 aids in preventing injury to surrounding tissue; additionally, migration of the wire is prevented.

While specific embodiments of the invention have been shown and described, the invention should not be considered as limited to these embodiments, but only as limited by the appended claims.

I claim:

1. A cap for use in conjunction with a wire employed for holding bones following placement of said bones for healing purposes, said cap being adapted to be placed on an exposed end of said wire and providing for location of said wire and protection from the exposed end of said wire, the cap being in the form of a covered, press-on cap.

2. The cap of claim 1 wherein said cap is in the form of a wire coil.

3. The cap of claim 2 wherein the diameter of said wire coil tapers from an open end to a closed end.

4. A process for setting one or more bones, said bones being surrounded by tissue, including skin, including:
   a. placing the pieces of said bone in proper juxtaposition for healing;
   b. inserting through at least two pieces of said bone a wire to hold said pieces in place;
   c. allowing one end of said wire to protrude from said bone, but to lie within the tissue and skin surrounding said bone;
   d. removing any sharp end from said protruding portion; and
   e. applying to said blunted end a covered, press-on cap to provide for location of and protection from the end of said wire.

* * * * *